(12) United States Patent
Rafalovich et al.

(10) Patent No.: US 11,065,479 B1
(45) Date of Patent: Jul. 20, 2021

(54) PORTABLE AIR POWERED RESPIRATOR

(71) Applicants: Alexander P Rafalovich, Sarasota, FL (US); Vladimir G Bulygin, Saint-Petersburg (RU); Daniil V Golubev, Saint-Petersburg (RU); Vladislav K Spiridonov, Saint-Petersburg (RU)

(72) Inventors: Alexander P Rafalovich, Sarasota, FL (US); Vladimir G Bulygin, Saint-Petersburg (RU); Daniil V Golubev, Saint-Petersburg (RU); Vladislav K Spiridonov, Saint-Petersburg (RU)

( * ) Notice: Subject to any disclaimer, the term of this patent is extended or adjusted under 35 U.S.C. 154(b) by 0 days.

(21) Appl. No.: 16/995,887

(22) Filed: Aug. 18, 2020

(51) Int. Cl.
*A62B 7/10* (2006.01)
*A61L 9/16* (2006.01)
*A61L 9/20* (2006.01)
*A62B 7/04* (2006.01)
*A62B 17/04* (2006.01)

(52) U.S. Cl.
CPC ...... *A62B 7/10* (2013.01); *A61L 9/16* (2013.01); *A61L 9/20* (2013.01); *A62B 17/04* (2013.01); *A61L 2209/12* (2013.01); *A61L 2209/14* (2013.01)

(58) Field of Classification Search
CPC ..... A62B 7/10; A62B 7/04; A61L 9/16; A61L 9/20
See application file for complete search history.

(56) References Cited

U.S. PATENT DOCUMENTS 6,014,971 A * 1/2000 Danisch ............... A62B 18/045
128/201.25

* cited by examiner

*Primary Examiner* — Kevin Joyner

(57) ABSTRACT

Unlike the existing powered air-purifying respirators (PAPR) that are bulky, heavy, and expensive the invention offers a light-weighted inexpensive portable PAPR consisted of a single piece secured on user's head. The respirator is for use in contaminated environment including one with highly contagious viruses such as SARS-CoV-2 that causes COVID-19. A clear visor of the respirator protects eyes, nose, and mouth. The rest of the user's head protected with a soft airtight cover. A small fan or fans pump air through the filters. Because the fan capacity exceeds airflow required for breathing, air pressure under the cover is slightly higher than ambient pressure. It protects the visor and user glasses from fogging and prevents leaks through any looseness. A special port allows use of equipment and devices as a stethoscope for medics or oxygen supply for patients. Despite the respirator primarily targeted for medical personnel and patients, its convenience, 1 lightness and affordability allow usage by general population especially at the time of an epidemic or a pandemic.

16 Claims, 5 Drawing Sheets

US 11,065,479 B1

PORTABLE AIR POWERED RESPIRATOR

BACKGROUND OF THE INVENTION

The present invention relates to medical respirators specifically to air-purifying respirators that filter breathing air from respiratory droplets, particles, dust, microbes, bacteria, and other airborne microorganisms. The invention primarily could be used by medical personnel attending patients with contagious diseases and persons with infectious diseases as well as breathing, heart, and other problems especially at the time of an epidemic or a pandemic such as the latest outbursts of Ebola and COVID-19.

At the present time there are 2 types of filtering respirators: masks and air powered respirators, PAPR (Personal Air Powered Respirator). Both types of respirators have their limitations.

Majority of masks, that are quite simple and affordable respirators cover the mouth and the nose leaving the rest of face open to infections. That is especially dangerous for eyes exposed to droplets from coughs and sneezes and airborne bacteria. On the other hand, in masks wherein a clear glass or a visor added the visor may become completely fogged in a short time. Another problem with these respirators is the mask itself before long may get soaked with moisture absorbed from the user's exhale. This, in turn, may attract airborne particles and microorganisms to the mask. Besides, if the mask material or its filtering part works as a fine air filter that filters small airborne particles the user may find it difficult to breathe.

Existing PAPRs are also not perfect either for medical personal or for general population. As an example, consider popular 3M respirators. The respirator consists of a mask with a robust helmet, protecting the entire human head and separate air supply unit secured either on the user's back with straps or the waist with a waistband. Air supply units are equipped with a powerful fan driven with a 12-volt battery and connected to the mask with an expensive corrugated hose. Compared to simple masks it is advantageous that 3M PAPRs can filter ambient air with fine filters. However, these PAPRs are expensive with the price tag exceeding $1500 and for some models even $2000, and can also be heavy and bulky, as well as require large capacity batteries. Besides, the user's glasses hardly fit inside the mask, powerful fan warms up breathing air by several degrees and, in addition, there is considerable inconvenience in disinfection of parts required after each use.

The present invention eliminates listed disadvantages with a respirator that is energy efficient, inexpensive, reliable, universal, and convenient for disinfection. The presented portable PAPR type respirator is for multiple use and capable of comprehensive air cleaning from liquid droplets, dust, microbes, bacteria, and other airborne pathogens without any significant increase of air temperature.

SUMMARY OF THE INVENTION

In one embodiment of the invention a portable air powered respirator for cleaning and disinfection of breathing air from substances harmful for humans consists of a personal mask with the main parts consisting of a frame, a visor, and supporting strips, the frame positioned on the upper part of the user's head supporting and carrying most of the respirator parts and systems including the visor from transparent material that attached to the front of the frame and situated at some distance from the user's face allowing user to put on glasses, the visor that provides an unabstracted view while isolating eyes, nose, mouth, and at least a part of the forehead, and the strips attached to the frame positioning and supporting the respirator on user's head, situated on the frame a system for filtration, purifying and delivering clean air for breathing, the system including suction replaceable filters, a small battery-powered fan, an air hose delivering clean air to the under-mask space for breathing, and a suction compartment that houses the fan mounted on vibration damping spacers, vents for venting of exhaled air and excesses of supply air pumped by the fan while maintaining pressure under mask that is slightly higher than the atmospheric pressure with either calibrated orifices, or venting filters, or venting check valves, or combination of filters, check valves, and orifices located either on the airtight cover, or on a part of the frame, elements of an electrical system providing power to the fan and situated on and around the frame including a battery, an on/off switch, connectors, and wiring, a soft airtight cover insulating under-mask space and protecting parts of the head not covered by the mask from untreated air, the cover spreading from the top of the personal mask down to neck or shoulders with seals around the visor, vents, filters, and neck or shoulders.

According to another embodiment the respirator also comprises straps for a chin and/or an occiput support and adjusting mechanism for convenience and to secure the mask immobility while user turns or tilts the head.

According to another embodiment there is a special port for devices and/or equipment required for work and/or life the port providing insulation of the parts inside of under mask-space from ambient that allows safe usage of, for example, stethoscope for medical personal or oxygen flow for a diseased person.

Yet according to another embodiment the system for filtration, purification and delivering clean air for breathing equipped with the suction filters mounted on the outside surface of the suction compartment or a lid of this compartment and are either fine mechanical filters or a combination of mechanical and electrostatic-based filters, or mechanical filters capable to have electrostatic charge destroying harmful viruses and bacteria.

According to another embodiment the walls of the suction compartment, for example lid walls can, at least partly, be substituted with special suction filters. It increases the overall filter frontal surface, reduces velocity, pressure drop, fan power, and suction noise.

According to another embodiment to balance the weight of the visor attached to the frontal part of the frame the battery, the fan and the suction compartment with the filters situated on the back, occipital part of the frame.

According to another embodiment the visor of the personal mask could have a different shape. If a user needs an undistorted frontal view, the frontal part of the visor is either flat or curved with a large radius while side parts of the visor made either as separate flat pieces or bent from the flat front with small radius. This type of the visor could be beneficial for surgeons, as an example. The visor with flat frontal panel could be convenient for projecting images from fiber bronchoscope or other fiber scopes with the help of Smart Glasses technology such as Google Glasses or Intel's Vaunt. If a surgeon needs to see the image from an eyepiece the visor may have an orifice matching the eyepiece with a plug for closing. To provide a broader view that includes sides, the frontal part of the visor could be curved with smooth transition to the side parts.

Yet another embodiment includes a latch on the side or/and on the back of the mask allowing an adjustment of the visor tilt.

Another embodiment includes a method of delivering air for breathing in a way the airflow first hits the top part of the visor thus protecting the visor from fogging.

Another embodiment offers the cover with a separate top and a bottom, both made with airtight cloth. The top cloth mounts on the top part of the frame, and the bottom attached to the frame bend. Air hoses delivering breathing air can be made from noise-absorbing material attached to the longitudinal part of the mask frame or the top cloth. The holes for mounting venting filters or venting check valves can be located either on the frame, or the airtight cover, or on a part of the visor not obstructing the view.

Yet according to another embodiment the soft cover provided with special pockets for user fingers that impowers the user with ability to manipulate devices, equipment, and glasses located in under-mask space with her/his fingers.

Another embodiment includes a control notifying user of the batteries charge level and alerting user when the charge drops below a predetermined level.

Another embodiment includes positioning of germicidal UV lamps at the air intake for disinfection—for example, while the battery is being charged the filters, the fans, the internal part of the mask, and other parts of the breathing air passage are disinfected.

Another embodiment of the invention considers the respirator that is capable providing evaporating cooling in hot climate. This respirator includes a coaxial air hose with the inner hose assigned to flowing purified and disinfected air, while the outer hose is for water. The inner hose walls made with water-absorbing material. Through a special port the outer hose supplied with distilled water. While the respirator is in operation the water absorbed by the inner hose walls evaporates from the inner side of the inner hose reducing air temperature and increasing humidity of air delivered for breathing.

BRIEF DESCRIPTIONS OF THE DRAWINGS

DESCRIPTION OF THE PREFERRED EMBODIMENTS

It is understood that the invention is not limited to all details of the design examples presented herein and the details may vary as the skilled person will recognize. It is also understood that terminology used herein is only for particular embodiments description and is not intended for limiting scope of the invention. Use of singular forms "a", "an", and "the" herein and in claims does not exclude plural reference until the context clearly indicates otherwise. Also use of plural forms with words ending with "s" or "es" does not exclude a singular reference until the context indicates otherwise. For example, a reference to "a fan" is a reference to one or more fans and a reference to "filters" is a reference to one or more filters.

Figure 1:
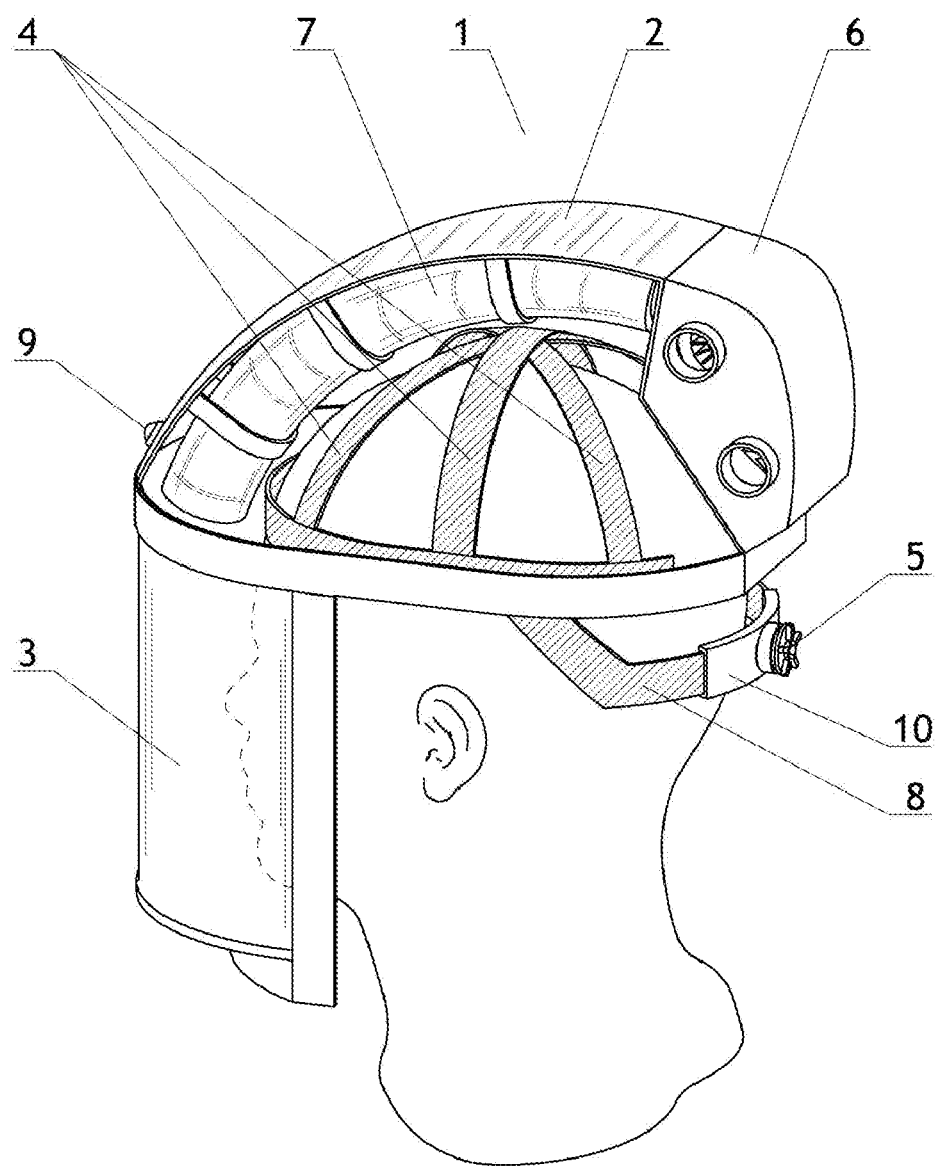
FIG. 1 depicts a side view of the personal mask of the portable respirator.
Figure 4:
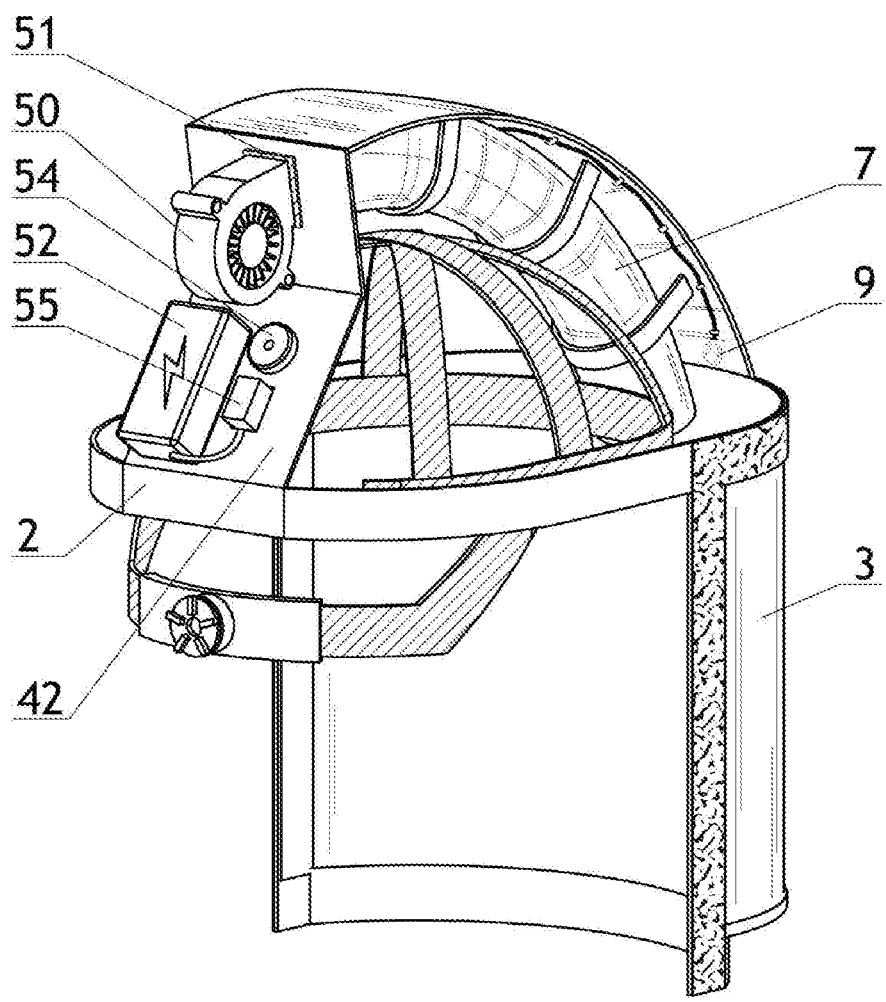
FIG. 4 illustrates positioning of the fan providing purified and disinfected air for breathing, the hose delivering clean air, and main elements of the electrical supply.

FIG. 1 demonstrates a respirator without a soft cover. A personal mask 1 includes a frame 2, a visor 3, non-rigid straps 4 supporting the mask on the user's head. Straps 8 with an occiput support 10 and adjusting mechanism 5 secure immobility of the mask while user turns or tilts the head. Additional straps could also be attached to the user's chin. To provide side vision visor 3 could be made either as a curved single piece of clear material or assembled from separate frontal and side parts. In both cases the visor design provides satisfactory space allowing user's personal glasses inside the mask. In addition, visor 3 could be provided with a tilt mechanism with a latch. The mask 1 also includes a system for filtration, purifying and delivering clean air for breathing, example of which is shown in FIG. 4. The system includes a fan for delivering air, filters for air purification and disinfection, and an air hose 7 delivering air to the visor. The hose 7 could be manufactured with noise-absorbing material.

If the respirator is being used in high temperature conditions air temperature could be reduced with evaporating cooling. In this case, air hose 7 is coaxial with inner hose for flowing purified and disinfected air, while the outer hose is for water. The inner hose walls made with water absorbing material. Through a special port the outer hose supplies distilled water absorbed by the inner hose walls. While the respirator is in operation the water evaporates from the inner side of the inner hose reducing air temperature and increasing humidity of air delivered for breathing.

A lid 6 that carries the filters covers the fan of the air purification and delivery system secured to the frame 2 ether with a latch or clamp in a way that lid 6 can be easily detached from the frame allowing access to parts attached to the frame. Most elements of an electrical system that consists of a battery, a switch, wiring, a charging port, and connectors could be situated together with the fan under lid 6 while a battery charge indicator 9 is on the front part of the mask, enabling the user to see the battery charge level.

Figure 2:
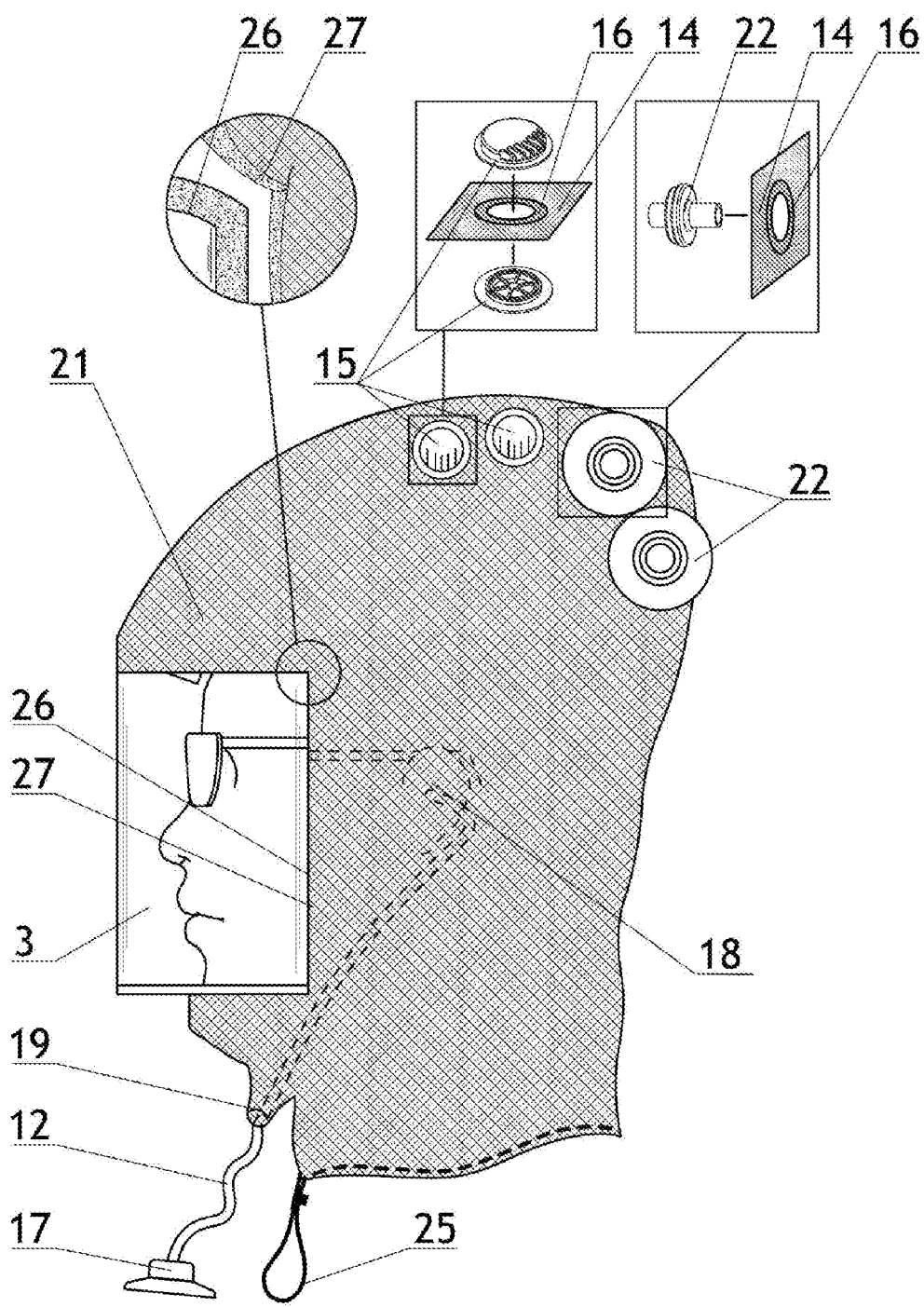
FIG. 2 shows a side view of the air-powered respirator per FIG. 1 with soft airtight cover.

FIG. 2 shows cover 21, suction filters 22 and outlet ports with check valves 15. Cover 21 is made from soft airtight material sealed around user's neck or shoulders with a sealing lace 25. Perimeter of the visor 3 is sealed with cover 21, for example, with Velcro type seals 26, 27. For breathing air exhaust also as the air excess release either calibrated orifices, or venting filters, or check valves 15, or combinations of orifices, filters and check valves could be installed and sealed in the outlet ports. FIG. 2 shows an example of securing suction filters 22 and check valves 15 on the cover 21 with pads 14 and silicone airtight seals 16. Sealing of the visor, filters and valves allows keeping cover 21 under pressure that slightly exceeds the ambient pressure. This, in turn, prevents unpurified ambient air to get into the under-mask space.

For medical personal there is a need to use special equipment, a part of which is in the under-mask space, without fear of contaminated air getting inside of the under-mask space. FIG. 2 depicts a stethoscope with a chest piece 17 outside, earpieces 18 inside of the mask and flexible tubing 12 sealed in a special port 19. Flexible fabric of cover 21 allows the user to take earpieces 18 in and out of ears. For convenience, special pockets for fingers could be added to cover 21. Besides of medical devices port 19 could be also used for other purposes, for example, for delivering oxygen to a diseased person needing it for special procedures or for breathing.

Figure 3:
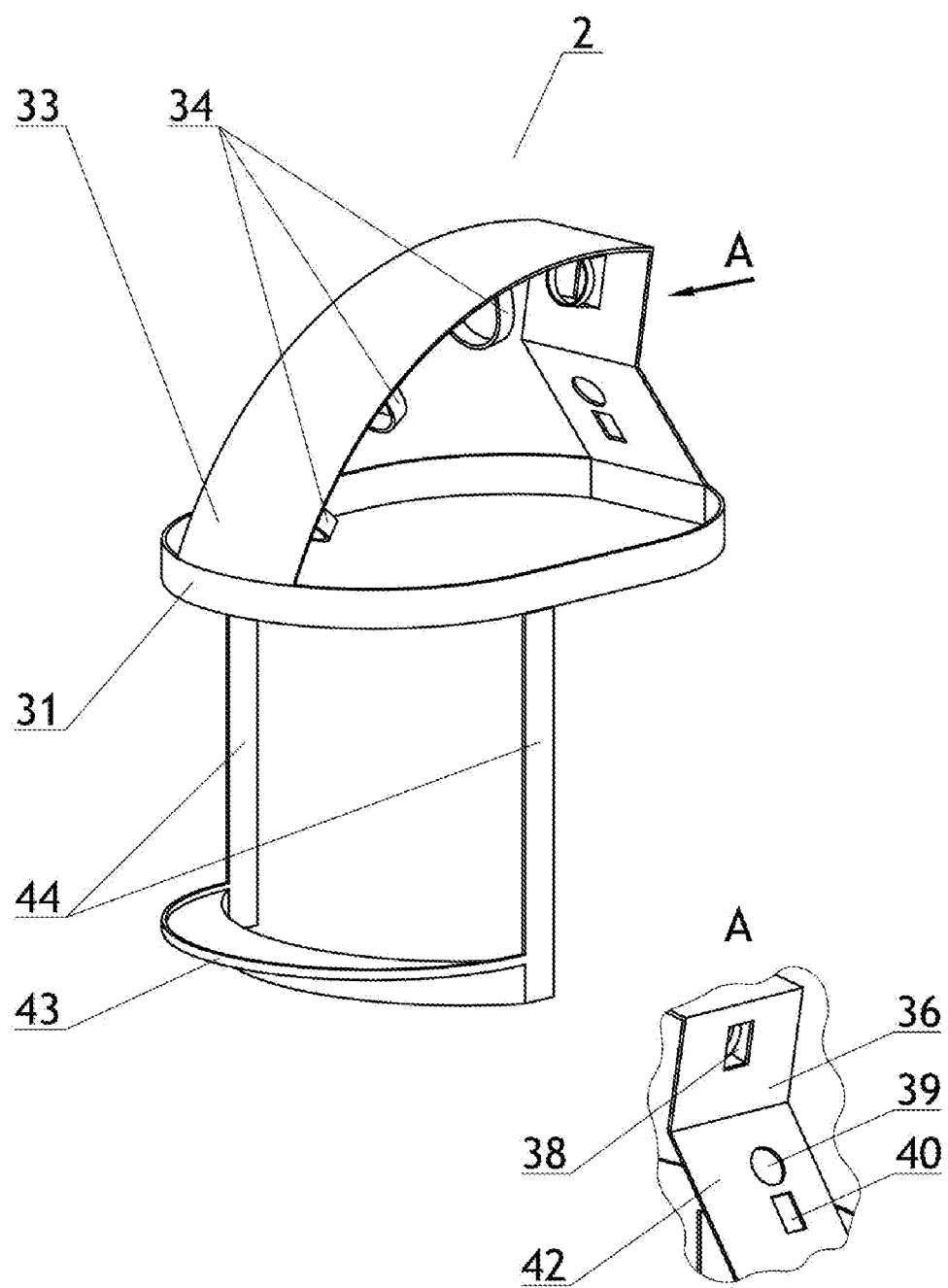
FIG. 3 depicts the mask-supporting frame which carries most of the parts of the respirator as it is shown in FIG. 1, 2.

FIG. 3 shows frame 2 that consists of a bend 31 positioned on the upper part of the user's head, a longitudinal strip 33 connected with the front and back of the bend 31. Inner part of strip 33 houses hose 7 supported from the bottom with straps 34. Vertical or slightly inclined surface 36 serves as the base on which the fan is mounted. Electrical on/off switch for fan motor is located on plane 42. An opening 39 in plane 42 is for a charging connector of the battery, a port 40 is for electrical switch actuator turning switch on/off. The visor 3 installed between bend 31, support 43, and vertical posts 44.

FIG. 4 demonstrates a view of the mask without airtight cover 21 and lid 6. It shows assembly of the fan 50 installed on a vibration damping gasket 51, electrical battery 52, switch 54, and charging connector 55 on plane 42 of frame 2.

Figure 5:
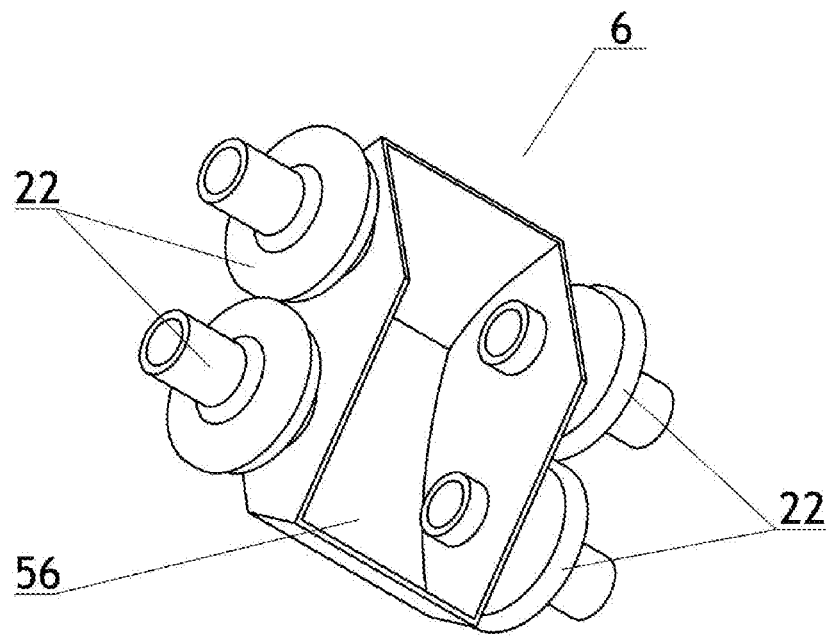
FIG. 5 shows the lid with suction filters, covering fan and electrical supply parts and together with the bottom plane on the back of the frame forms the air suction compartment.

FIG. 5 shows lid 6 with suction filters 22. Opening 56 in the lid serves as an air suction compartment aligning airflow after filters and reducing pressure drops, vibration, and sound. In alternative design specially designed filter or filters with larger frontal section substitute at least a part of the lid structure serving as a piece of the lid wall. Beside of air velocity reduction these filters would not have sharp expansion of exiting from filters air, thus avoiding considerable pressure losses.

The respirator works as follows. First, a user put the mask on the head and adjust it for convenience. If the switch actuator located on the inner side of the mask, user turns on the switch starting the fan, then puts the respirator on the head. If the switch is on the outer side of the mask, user can start the fan after putting the respirator on. After the fan starts suction pressure drops below atmospheric and ambient air begins flowing to suction compartment 56 through filters 22. After suction filters purified and disinfected air pumped by the fan through air hose 7 reaches the visor and then user's nose and mouth. During the operation, the fan pumps more air that necessary for breathing, thus, the under-mask pressure is always slightly higher than atmospheric. That, in turn, protects user from breathing of unpurified air that could leak under mask through any looseness. Exhaled air mixed with excesses supplied by the fan leave under-mask space via check valves, calibrated orifices, or venting filters back to ambient. Main advantage of having at least one venting filter in air outlet is that in case of the fan failure the user for a while could inhale air purified by this filter. Main reason for the fan failure is lack of the battery charge. There is the charge indicator 9 in the respirator warning the user when battery charge drops near the level that could bring the fan stoppage.

What we claim are:

1. A portable air-powered respirator for personal use, the respirator for cleaning and disinfection of ambient air from substances causing infectious diseases in humans, the respirator comprising:

A personal mask comprising a frame, a clear visor, and supporting strips, the frame positioned on an upper portion of a user's head supporting and carrying the visor;

Said visor formed from a transparent material, said visor attached to the front of the frame and situated at a distance from the user's face allowing the user to put on glasses, the visor providing an unobstructed view while isolating the user's eyes, nose, mouth, and at least a part of the forehead;

Said supporting strips attached to the frame and positioned to support the respirator on the user's head;

A system for filtration located on the frame, said system purifying and delivering clean air for breathing, the system including replaceable suction filters, a battery-powered fan, an air hose delivering clean air to an under-mask space for breathing, and a suction compartment that houses said fan mounted on vibration damping spacers;

Vents for venting of exhaled air and excesses of supplied air pumped by the fan to ambient while maintaining pressure in the under-mask space higher than atmospheric pressure, said vents including at least of:

one or plurality of venting filters, calibrated orifices, venting check valves, or combination of one or a plurality of filters, check valves and calibrated orifices;

An electrical system providing power to the fan, said electrical system situated on and around the frame, said electrical system comprising;

A battery, an on/off switch, connectors, and wiring;

A soft cover insulating the under-mask space and protecting a portion of the user's head not covered by the mask from untreated air, the cover spreading from the top of the user's head down to the user's neck or shoulders with seals around the visor, the vents, the suction filters, and the neck or shoulders; and A sealed port for devices and/or equipment required for work and/or for lifesaving measures, the sealed port located in the soft cover providing insulation of the devices and/or the equipment inside of the under-mask space from ambient, thus allowing safe usage of a stethoscope and other medical devices and/or equipment for medical personnel.

2. The respirator of claim 1, further comprising straps for the user's chin and/or the user's occipital support and adjusting mechanism that secures the mask immobility while the user turns or tilts the head.

3. The respirator of claim 1, wherein the suction filters mounted on the outside surface of the suction chamber and are either fine mechanical filters, or combined mechanical and electrostatic-based filters, or mechanical filters that use electrostatic charge for destroying harmful viruses and bacteria.

4. The respirator of claim 3, wherein the suction filters are at least a part of the suction compartment housing.

5. The respirator of claim 1, wherein the battery, the fan, and the suction compartment with the suction filters situated on the back, occipital part of the frame.

6. The respirator of claim 1, comprising a battery charge indicator located on the personal mask and alerting the user when the battery charge drops below a predetermined level.

7. The respirator of claim 1, wherein the frontal part of the visor is either flat or curved with a large radius while the side parts of the visor are made either as separate flat pieces or bent from the flat front with a small radius.

8. The respirator of claim 1, wherein the frontal part of the visor curved with a radius providing smooth transition to the side parts.

9. The respirator of claim 1, wherein the user could get images on the visor from a fiber bronchoscope or other fiber scopes projected on the visor with the help of a smart glasses technology.

10. The respirator of claim 1, further comprising a tilt mechanism with a latch on the side or/and on the back of the mask allowing of changing of the visor tilt.

11. The respirator of claim 1, wherein the air hose delivering breathing air is made from a noise-absorbing material.

12. The respirator of claim 1, wherein the air hose delivers breathing air to the under-mask space in a way that the airflow first reaches the top part of the visor, thus protecting the visor from fogging.

13. The respirator of claim 1, wherein water evaporates into disinfected and/or cleaned air for controlling breathing air temperature and humidity.

14. The respirator of claim 13, comprising the air hose delivering breathing air and containing a water-absorbent material for absorbing distilled water provided through a special water-supply port, and while the respirator is in operation, water absorbed by the water-absorbent material evaporates, thus reducing the temperature and increasing humidity of breathing air.

15. The respirator of claim 1, wherein the soft cover is provided with pockets for user's fingers enabling the user to manipulate devices, equipment, and glasses located in the under-mask space.

16. The respirator of claim 1, further comprising of germicidal UV lamps at the air intake for additional air purification while the respirator is in operation and/or for disinfection of the venting filters, the fan, the internal surface of the visor, and other parts and surfaces that are in the under-mask space while the respirator is being disinfected and/or while the battery being charged.

* * * * *